United States Patent [19]

Dawans et al.

[11] Patent Number: 5,443,712

[45] Date of Patent: Aug. 22, 1995

[54] DEVICE FOR DETECTING POLLUTANT TRACES IN AN AQUEOUS MEDIUM

[75] Inventors: François Dawans; Michel Huvey, both of Bougival; Jean Lesage, Elancourt, France

[73] Assignee: Institut Francais du Petrole, Rueil Malmaison, France

[21] Appl. No.: 226,831

[22] Filed: Apr. 13, 1994

[30] Foreign Application Priority Data

Apr. 13, 1993 [FR] France ................. 93 04418

[51] Int. Cl.⁶ ........................................... G01N 27/26
[52] U.S. Cl. ........................... 204/400; 204/153.1; 204/153.22; 73/40; 73/73; 73/53.01; 73/61.41; 73/61.43; 324/514
[58] Field of Search ................ 204/400, 153.1, 153.22; 73/40, 53.01, 61.41, 61.43; 324/514

[56] References Cited

U.S. PATENT DOCUMENTS

| | | | |
|---|---|---|---|
| 3,427,869 | 2/1969 | Karlbom | 73/73 |
| 3,720,797 | 3/1973 | Gunn et al. | 73/61.41 |
| 4,058,802 | 11/1977 | Meyers | 73/61.41 |
| 4,125,822 | 11/1978 | Perren et al. | 324/514 |

FOREIGN PATENT DOCUMENTS

| | | |
|---|---|---|
| 2254749 | 7/1975 | France . |
| 2266157 | 10/1975 | France . |
| 2455294 | 11/1980 | France . |
| 2559233 | 7/1977 | Germany . |
| 3140804 | 4/1983 | Germany . |

*Primary Examiner*—John Niebling
*Assistant Examiner*—Bruce F. Bell
*Attorney, Agent, or Firm*—Antonelli, Terry, Stout & Kraus

[57] ABSTRACT

The present invention relates to a device for detecting traces of hydrocarbon-containing pollutants present in an aqueous medium, comprising an electric circuit including at least one sensitive element reacting through degradation to the presence of said pollutants, electric means co-operating with said sensitive element and a means for checking the condition of said circuit.

According to the invention, said electric means include at least two contactors holding said sensitive element in compression.

FIG. 1 to be published.

6 Claims, 1 Drawing Sheet

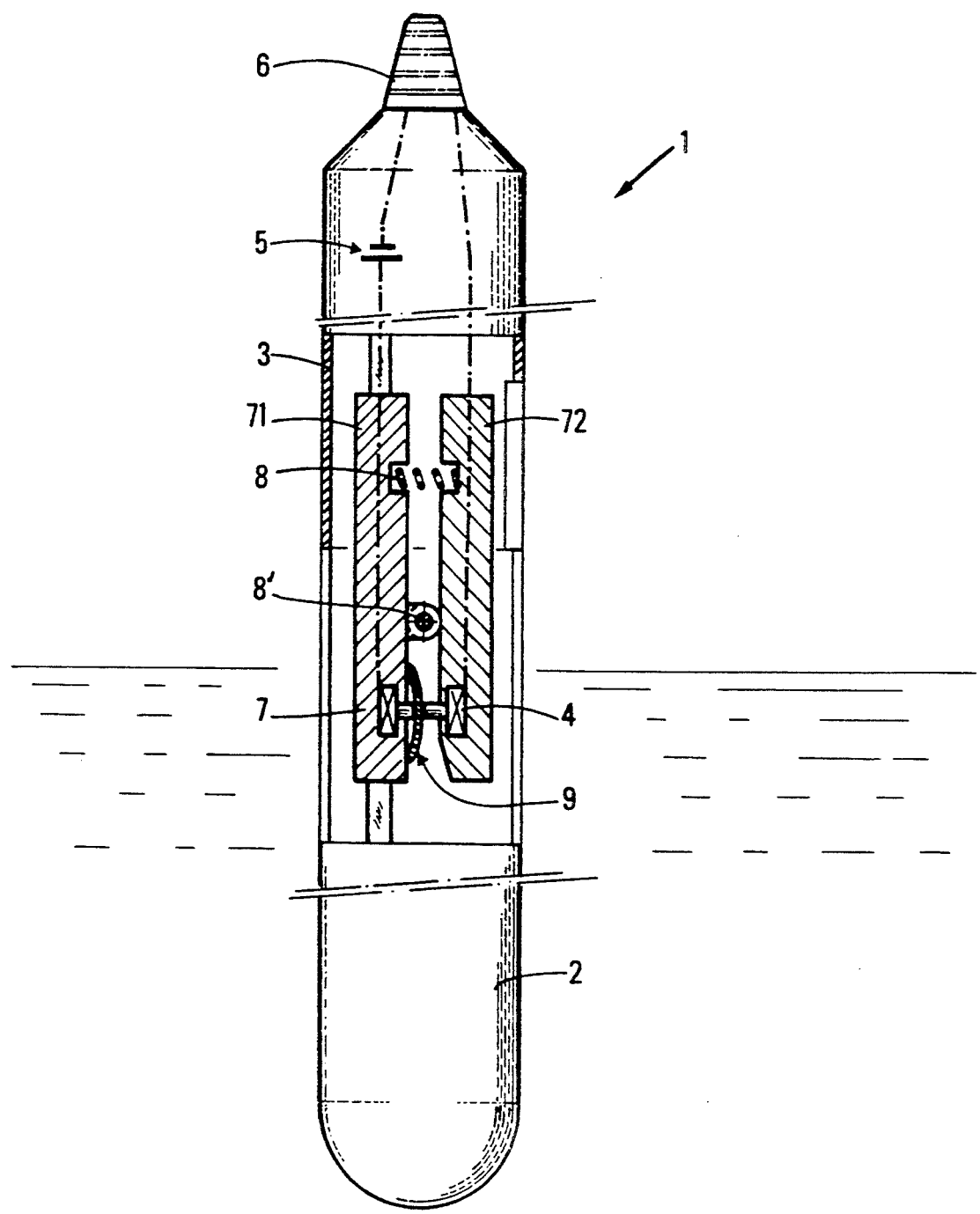

DEVICE FOR DETECTING POLLUTANT TRACES IN AN AQUEOUS MEDIUM

BACKGROUND OF THE INVENTION

The present invention relates to a device for prevention of pollution in an aqueous medium.

More particularly, the present invention relates to a device for detecting certain organic pollutants, notably hydrocarbons, present in an aqueous medium.

In this field, there are well-known detection systems including at least one element sensitive to the pollutant which deteriorates or, more generally, whose mechanical properties change in contact with the pollutant.

The working principle of such detection systems, which is well-known, consists in making the sensitive element co-operate with means capable of activating an alarm when the sensitive element is deteriorated by the pollutant.

According to the applications considered, a sound or a visual alarm signal, or any other reaction means, may be activated as a result of the degradation of the sensitive element.

The degradation of the sensitive element may, for example, trigger off the scattering of an absorbing or a neutralizing product with respect to the pollutant.

Automatic detection devices sensitive to certain pollutants, notably hydrocarbons, and comprising two pieces of a band or of a wire glued together with a special glue which is deteriorated or dissolved by the pollutant, have already been proposed. The assembly being kept under stress, the action of the pollutant causes the assembly to break, which leads to the activating of an alarm signal. Such devices have, for example, been manufactured by the Canadian company Bennett Pollution Controls Ltd under the trade name "Oil Spill Detection System".

Such a system entails manufacturing difficulties and the results are little reliable as the sensitivity of the gluing to the pollutants greatly depends on the manufacturing quality.

Other known devices are based on the use of a massive sensitive element which is caused to swell or is destroyed in contact with the pollutants, which leads to the activating of an alarm (see French patent No. 2,178,950).

Various products which have been proposed so far for making up the sensitive element are not completely satisfactory as they appear to be too little sensitive to pollutants (products according to French patent No. 2,178,950) or, when their sensitivity is sufficient, they do not withstand the action of light long enough (products according to French patent No. 2,254,749).

In order to remedy some of the drawbacks stated above, it has been proposed, in French patent FR-2,455,294 corresponding to U.S. Pat. No. 4,351,642, to use as a material deteriorating in contact with the products, a material comprising a butadiene-styrene sequential copolymer at least part of which is hydrogenated. Preferably, this material includes stabilizing agents with respect to ultraviolet rays, antioxidant agents and 400 k oil in proportions determined according to the use envisaged.

According to this embodiment, the sensitive element may be a thin band kept under traction and whose breaking, due to its deterioration by hydrocarbons, activates an alarm system.

It turned out that such a hydrocarbon detector is really active only in the presence of a certain amount of hydrocarbons in water. This detector acts above all as a fuse which is released only by the presence of large amounts of hydrocarbons.

SUMMARY OF THE INVENTION

In order to remedy notably this problem, the present invention proposes a detector for hydrocarbons present in an aqueous medium, whose sensitivity is distinctly improved with respect to the prior art, and which therefore allows hydrocarbon traces dissolved in an aqueous medium to be detected.

The simplicity of the device is another advantage of the invention. The small amount of material making up the sensitive element represents an additional advantage of the invention.

The present invention may thus be used for detecting the pollution of groundwater tables.

Another possible use of the invention relates to the permanent monitoring of sea, fluvial, port, coastal, urban, industrial or rain waters against hydrocarbon traces pollution.

The invention may be used for detecting oxygenated hydrocarbons such as phenols, acids, ethers, esters, etc.

The object of the present invention is to propose a device for detecting traces of pollutants present in an aqueous medium, comprising at least one sensitive element reacting through degradation to the presence of hydrocarbons, an electric circuit including electric contact means co-operating with said sensitive element and a means for checking the condition of the circuit.

According to the invention, said electric contact means consist of at least two contacts holding said sensitive element in compression.

Preferably, the thickness of the sensitive element at the level of the compression zone ranges between 0.05 mm and 0.60 mm.

The sensitive element advantageously consists of a thermoplastic elastomer which is not chemically cross-linked.

More precisely, the sensitive element consists of a butadiene-styrene multisequential copolymer.

Furthermore, the device according to the invention may include a safety element stopping the flow of electricity (in the electric circuit) in case the device is no longer immersed.

According to an embodiment of the invention, at least one of the contacts co-operating with the sensitive element exhibits an indentation at the level of the sensitive element.

BRIEF DESCRIPTION OF THE DRAWING

Other features and advantages of the invention will be clear from reading the description hereafter given by way of non limitative examples, with reference to the accompanying sole FIGURE.

This FIGURE diagrammatically shows by way of example a device 1 for detecting hydrocarbon traces floating on the water surface.

DESCRIPTION OF THE PREFERRED EMBODIMENTS

This device may be held in a vertical position by means of a ballast 2. A casing 3 contains an electric circuit mainly including in series two electrical contacts 4, a self-contained electrical supply 5 and a means for checking the condition of the circuit such as a sound and/or a light alarm signal. An additional safety element (not shown) may be provided in order to prevent possible electric arcs in case the contacts are no longer immersed in water.

The contacts are compressed one against the other by any means 7 known in the art. According to the example shown in the FIGURE, this means 7 looks like a pair of pliers provided with two arms 71, 72 articulated around a pin 8' and two ends of which are compressed by a spring 8 intended to push back the two ends located on the other side of pin 8'. Without departing from the scope of the invention, means 7 may consist of a torsion spring located between the two arms 71, 72 and providing both connection between the two arms and compression of two ends against one another. Arms 71, 72 are made of an insulating material and they include each at least one housing for a contractor 4 and passages for electric wires connecting each contact to the other components of the electric circuit.

Each contact 4 preferably exhibits an indentation or salient zone of rounded or cylindrical shape in order to increase the pressure on the material, the load being then lumped and not distributed.

Any means capable of adjusting the compression stress exerted on the sensitive element may be advantageously provided.

A sensitive element 9, in the form of a thin film, whose thickness preferably ranges between 0.05 mm and 0.60 mm, is interposed between the two contactors 4 at the level of the indentation when there is one.

Setting of the sensitive element 9 is achieved through any conventional technique of laying of a thin film or of a coating obtained after the evaporation of the solvent initially present in a polymer in solution.

The sensitive element 9 preferably consists of a non crosslinked thermoplastic elastomer such as, for example, a butadiene-styrene multisequential copolymer.

The sensitive element decays, as it is well-known in the art, in the presence of hydrocarbons.

According to the invention, this degradation is promoted by the fact that the sensitive element 9 is kept in compression between the two contacts 4.

When the device according to the invention is placed in a non polluted water, sensitive element 9 does not decay and therefore no contact is established, alarm 6 is not activated.

When the device according to the invention is placed in a water containing a hydrocarbon, sensitive element 9 creeps little by little. The creep is accelerated by the fact that sensitive element 9 is compressed; the material therefore tends to lose its hardness as it absorbs hydrocarbons.

Thus, after a short time interval (specified in the examples hereafter), and even in the presence of slight hydrocarbon traces, alarm 6 may be activated.

Of course, the response time, i.e. the time after which the alarm is activated, varies according to the hydrocarbon concentration of the aqueous medium, the temperature of the aqueous medium, the nature of the sensitive material and its thickness: the examples hereafter show the influence of these parameters.

It is also possible to adjust this response time through the compressive stress exerted at the level of contacts 4, and/or through the shape and the dimensions of the indentation of the contactors.

The materials and the shapes of the various constituents of the device according to the invention will be selected so as to eliminate any electrolysis phenomenon which might result from the flow of current between contactors 4 inside the aqueous phase.

The following examples notably highlight the reliability of the system according to the invention, its sensitivity and the influence of the various parameters cited above.

EXAMPLE 1

A device is achieved according to the diagram of the appended FIGURE.

The power supply is a 4.5 V cell.

The detection signal is a light signal.

The electric detection contacts ($\phi = 3$ mm) are kept in compression under a 2 MPa stress, a (0.60 mm thick) polymer film being inserted between the contactors.

The device is immersed in pure water.

After three months, no flow of current is detected between the two contactors.

EXAMPLE 2

Example 1 is repeated by replacing the 0.60 mm thick membrane by a 0.12 mm thick membrane.

After three months, no flow of current has been detected.

EXAMPLE 3

Example 1 is repeated by immersing the system according to the invention in toluene-saturated water, i.e. containing about 0.05 g of toluene per 100 g of water.

The time after which alarm 6 is activated ranges between 24 and 48 hours.

EXAMPLE 4

Example 2 is repeated by immersing the system according to the invention in toluene-saturated water such as that defined in example 3.

The response time ranges from 10 to 17 hours.

EXAMPLE 5

Example 4 is repeated by replacing the 0.12 mm thick membrane by a 0.08 mm thick membrane.

The response time ranges from 4 to 5 hours.

EXAMPLE 6

Example 5 is repeated, the aqueous medium being kept at 50° C.

The response time is divided by 2.

Of course, the device which has been described may be provided with various modifications and additions by the man skilled in the art without departing from the scope of the present invention.

We claim:

1. A device for detecting traces of hydrocarbon-containing pollutants present in an aqueous medium which comprises at least one sensitive element that degrades in the presence of said hydrocarbon-containing pollutants in an aqueous medium, an electric circuit, electrical contacts within said electric circuit being in contact with said sensitive element, means for determining a flow of electricity within said circuit and means for pressing the contacts towards each other so that the sensitive element is held between the contacts in compression, the thickness of said sensitive element at a zone of compression ranging between 0.05 mm and 0.60 mm and said sensitive element being a film formed of a thermoplastic elastomer.

2. A device as claimed in claim 1, wherein the thermoplastic elastomer consists of a butadiene-styrene multisequential copolymer.

3. A device as claimed in claim 2, wherein said butadiene-styrene multisequential copolymer is at least partly hydrogenated.

4. A device as claimed in claim 1, further comprising a safety element for stopping the flow of electricity in the circuit in case the contacts are no longer immersed in the aqueous medium.

5. A device as claimed in claim 1, wherein at least one of the contacts cooperating with the sensitive element has an indentation at the zone of contact with the sensitive element.

6. A device as claimed in claim 1, further including means for adjusting the compressive force exerting on the sensitive element by said contacts.

* * * * *